US008738367B2

(12) United States Patent
Emori

(10) Patent No.: US 8,738,367 B2

(45) Date of Patent: May 27, 2014

(54) SPEECH SIGNAL PROCESSING DEVICE

(75) Inventor: Tadashi Emori, Tokyo (JP)

(73) Assignee: NEC Corporation, Tokyo (JP)

( * ) Notice: Subject to any disclaimer, the term of this patent is extended or adjusted under 35 U.S.C. 154(b) by 294 days.

(21) Appl. No.: 13/257,103

(22) PCT Filed: Feb. 18, 2010

(86) PCT No.: PCT/JP2010/001016

§ 371 (c)(1), (2), (4) Date: Sep. 16, 2011

(87) PCT Pub. No.: WO2010/106734

PCT Pub. Date: Sep. 23, 2010

(65) Prior Publication Data

US 2012/0004916 A1 Jan. 5, 2012

(30) Foreign Application Priority Data

Mar. 18, 2009 (JP) ................................ 2009-065443

(51) Int. Cl.

| | |
|---|---|
| ***G10L 15/00*** | (2013.01) |
| ***G10L 21/00*** | (2013.01) |
| ***G10L 21/02*** | (2013.01) |
| ***G10L 19/00*** | (2013.01) |
| ***G10L 19/12*** | (2013.01) |
| ***G10L 25/00*** | (2013.01) |
| ***G10L 25/93*** | (2013.01) |
| ***H03G 3/20*** | (2006.01) |
| ***H04R 3/00*** | (2006.01) |
| ***H04B 15/00*** | (2006.01) |
| ***H04R 25/00*** | (2006.01) |
| *A61F 11/06* | (2006.01) |
| *G10K 11/16* | (2006.01) |
| *H03B 29/00* | (2006.01) |

(52) U.S. Cl.

USPC ........... 704/200; 704/233; 704/226; 704/238; 704/208; 704/201; 704/240; 704/216; 704/214; 704/231; 704/221; 704/205; 704/273; 381/57; 381/110; 381/94.1; 381/92; 381/23.1; 381/71.1; 381/94.2

(58) Field of Classification Search

CPC ....... G10L 15/22; G10L 17/005; G10L 15/20; G10L 21/0208; G10L 15/10; G10L 19/12; G10L 19/10; G10L 25/93; G10L 15/08; G10L 25/78; H05K 999/99; G11C 2207/16; G10K 11/1788; H04R 3/005; H04R 29/00; H04R 25/552; H03G 3/32

USPC ......... 704/270, 233, 226, 200, 201, 238, 208, 704/240, 216, 214, 221, 273; 381/71.1, 58, 381/94.1, 94.2, 23.1, 92, 110, 57

See application file for complete search history.

(56) References Cited

U.S. PATENT DOCUMENTS 6,480,823 B1 * 11/2002 Zhao et al. .................... 704/226
6,570,991 B1 * 5/2003 Scheirer et al. ............... 381/110

(Continued)

FOREIGN PATENT DOCUMENTS

JP 2002-149190 A 5/2002
JP 2002-159086 A 5/2002

(Continued)

*Primary Examiner* — Paras D Shah

*Assistant Examiner* — Anne Thomas-Homescu

(74) *Attorney, Agent, or Firm* — Sughrue Mion, PLLC

(57) ABSTRACT

A speech signal processing device is equipped with a power acquisition unit, a probability distribution acquisition unit, and a correspondence degree determination unit. The power acquisition unit accepts an inputted speech signal and, based on the accepted speech signal, acquires power representing the intensity of a speech sound represented by the speech signal. The probability distribution acquisition unit acquires a probability distribution using the intensity of the power acquired by the power acquisition unit as a random variable. The correspondence degree determination unit determines whether a correspondence degree representing a degree that power acquired by the power acquisition unit in a case that a predetermined reference speech signal is inputted into the power acquisition unit corresponds with predetermined reference power is higher than a predetermined reference correspondence degree, based on the probability distribution acquired by the probability distribution acquisition unit.

17 Claims, 6 Drawing Sheets

(56) References Cited

U.S. PATENT DOCUMENTS

| | | | | |
|---|---|---|---|---|
| 6,768,979 | B1 * | 7/2004 | Menendez-Pidal et al. | 704/226 |
| 6,892,175 | B1 * | 5/2005 | Cheng et al. | 704/205 |
| 7,012,854 | B1 * | 3/2006 | Lo | 367/135 |
| 7,627,477 | B2 * | 12/2009 | Wang et al. | 704/273 |
| 8,098,843 | B2 * | 1/2012 | Kawaguchi et al. | 381/92 |
| 8,380,500 | B2 * | 2/2013 | Yamamoto et al. | 704/233 |
| 2002/0136238 | A1 * | 9/2002 | Hsiao et al. | 370/476 |
| 2002/0150265 | A1 * | 10/2002 | Matsuzawa et al. | 381/94.2 |
| 2002/0184014 | A1 * | 12/2002 | Parra et al. | 704/231 |
| 2002/0198704 | A1 * | 12/2002 | Rajan et al. | 704/214 |
| 2003/0004715 | A1 * | 1/2003 | Grover | 704/233 |
| 2005/0131689 | A1 * | 6/2005 | Garner et al. | 704/240 |
| 2005/0143982 | A1 * | 6/2005 | He et al. | 704/216 |
| 2005/0143988 | A1 * | 6/2005 | Endo et al. | 704/226 |
| 2005/0171773 | A1 * | 8/2005 | Iwahashi et al. | 704/240 |
| 2007/0073537 | A1 * | 3/2007 | Jang et al. | 704/233 |
| 2007/0258599 | A1 * | 11/2007 | Mao | 381/71.1 |
| 2008/0082320 | A1 * | 4/2008 | Popa et al. | 704/201 |
| 2008/0235013 | A1 * | 9/2008 | Kim et al. | 704/233 |
| 2008/0298599 | A1 * | 12/2008 | Kim | 381/58 |
| 2009/0063143 | A1 * | 3/2009 | Schmidt et al. | 704/233 |
| 2009/0125301 | A1 * | 5/2009 | Master et al. | 704/208 |
| 2009/0271187 | A1 * | 10/2009 | Yen et al. | 704/226 |
| 2010/0036659 | A1 * | 2/2010 | Haulick et al. | 704/226 |
| 2010/0150375 | A1 * | 6/2010 | Buck et al. | 381/94.1 |
| 2011/0051953 | A1 * | 3/2011 | Makinen et al. | 381/92 |
| 2011/0082690 | A1 * | 4/2011 | Togami et al. | 704/201 |
| 2011/0305345 | A1 * | 12/2011 | Bouchard et al. | 381/23.1 |
| 2012/0095753 | A1 * | 4/2012 | Nakajima et al. | 704/200 |
| 2012/0123772 | A1 * | 5/2012 | Thyssen et al. | 704/226 |
| 2012/0288106 | A1 * | 11/2012 | Bizjak | 381/57 |

FOREIGN PATENT DOCUMENTS

| | | | |
|---|---|---|---|
| JP | 2002-159098 | A | 5/2002 |
| WO | 2007/130766 | A2 | 11/2007 |

* cited by examiner

SPEECH SIGNAL PROCESSING DEVICE

CROSS REFERENCE TO RELATED APPLICATIONS

This application is a National Stage of International Application No. PCT/JP2010/001016 filed on Feb. 18, 2010, which claims priority from Japanese Patent Application No. 2009-065443, filed on Mar. 18, 2009, the contents of all of which are incorporated herein by reference in their entirety.

TECHNICAL FIELD

The present invention relates to a speech signal processing device that processes an inputted speech signal.

BACKGROUND ART

A speech signal processing device equipped with a plurality of microphones and configured to accept a speech signal inputted via each of the microphones and process the accepted speech signal is known.

As one of speech signal processing devices of this type, a speech signal processing device described in Patent Document 1 acquires, for each frequency, power (an amplification factor corresponding to power) representing the intensity of a speech sound represented by a speech signal accepted via a certain microphone. Then, the speech signal processing device determines whether power acquired at one moment (acquisition power) corresponds with predetermined reference power for each frequency. In the case of determining that the acquisition power does not correspond with the reference power, this speech signal processing device determines that the microphone is out of order.

[Patent Document 1] Japanese Unexamined Patent Application Publication No. JP-A 2002-159098

The plurality of microphones are arranged at mutually different positions. Therefore, the time when a speech sound generated at a certain position reaches each of the microphones varies with the microphone. In other words, at a certain moment, speech signals based on speech sounds generated at mutually different moments are inputted into the respective microphones.

Therefore, for example, in a case that the speech signal processing device is configured to use, as reference power, the power of a speech signal (a reference speech signal) accepted at a certain moment via a certain microphone (a reference microphone), there is fear that a speech signal as the source of acquisition power relatively largely differs from the reference speech signal.

In order to handle this, it is considered preferable to configure the speech signal processing device so as to use the average of power acquired at a plurality of moments as the acquisition power and the reference power.

Further, the power of background noise changes as time goes on. Therefore, also in a case that the speech signal processing device is configured to acquire the acquisition power and the reference power based on background noise, it is considered preferable to configure the speech signal processing device so as to use the average of power acquired at a plurality of moments as the acquisition power and the reference power.

However, in a case that the speech signal processing device is thus configured, for example, the speech signal processing device acquires the same acquisition power P0/N both when acquiring power P0 N-times and when acquiring power P1 smaller than the power P0 by a predetermined amount ΔP and power P2 larger than the power P0 by the predetermined amount ΔP N/2-times, respectively.

In other words, in this case, there is a problem that the speech signal processing device cannot determine with high accuracy whether power acquired when a predetermined reference speech signal is inputted corresponds with predetermined reference power.

SUMMARY

Accordingly, an object of the present invention is to provide a speech signal processing device capable of solving the abovementioned problem, "being incapable of determining with high accuracy whether power acquired when a predetermined reference speech signal is inputted corresponds with predetermined reference power."

In order to achieve the object, a speech signal processing device of an embodiment of the present invention is equipped with:

a power acquisition means configured to accept an inputted speech signal and, based on the accepted speech signal, acquire power representing intensity of a speech sound represented by the speech signal;

a probability distribution acquisition means configured to acquire a probability distribution with intensity of the acquired power as a random variable; and a correspondence degree determination means configured to determine whether a correspondence degree representing a degree of correspondence between the power acquired by the power acquisition means in a case that a predetermined reference speech signal is inputted into the power acquisition means and predetermined reference power is higher than a predetermined reference correspondence degree, based on the acquired probability distribution.

Further, a speech signal processing method of another embodiment of the present invention is a method including:

accepting an inputted speech signal and, based on the accepted speech signal, acquiring power representing intensity of a speech sound represented by the speech signal;

acquiring a probability distribution with intensity of the acquired power as a random variable; and determining whether a correspondence degree representing a degree of correspondence between the power acquired by input of a predetermined reference speech signal and predetermined reference power is higher than a predetermined reference correspondence degree, based on the acquired probability distribution.

Further, a speech signal processing program of another embodiment of the present invention is a program including instructions for causing a speech signal processing device to realize:

a power acquisition means configured to accept an inputted speech signal and, based on the accepted speech signal, acquire power representing intensity of a speech sound represented by the speech signal;

a probability distribution acquisition means configured to acquire a probability distribution with intensity of the acquired power as a random variable; and a correspondence degree determination means configured to determine whether a correspondence degree representing a degree of correspondence between the power acquired by the power acquisition means in a case that a predetermined reference speech signal is inputted into the power acquisition means and predetermined reference power is higher than a predetermined reference correspondence degree, based on the acquired probability distribution.

With the configurations of the present invention as described above, it is possible to determine with high accuracy whether power acquired when a predetermined reference speech signal is inputted corresponds with predetermined reference power.

EXEMPLARY EMBODIMENTS

Figure 1:
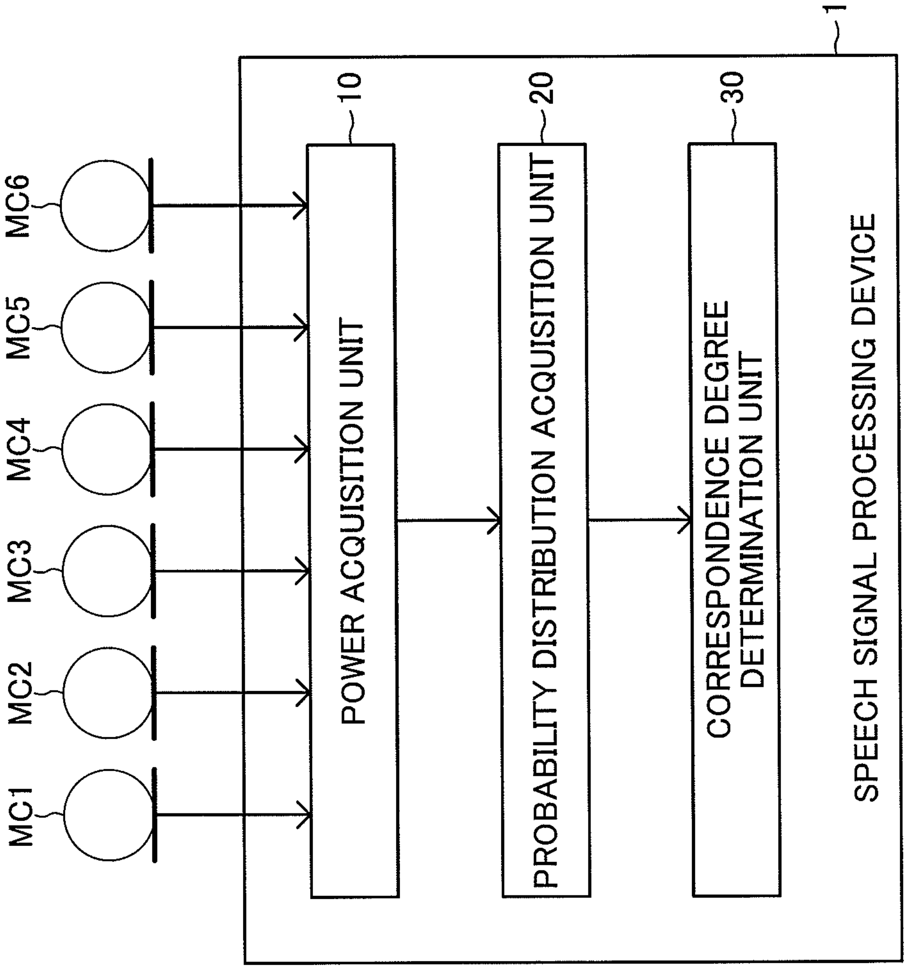
FIG. 1 is a block diagram schematically showing a function of a speech signal processing device according to a first exemplary embodiment of the present invention.

A speech signal processing device of an embodiment of the present invention is equipped with:

a power acquisition means configured to accept an inputted speech signal and, based on the accepted speech signal, acquire power representing intensity of a speech sound represented by the speech signal;

a probability distribution acquisition means configured to acquire a probability distribution with intensity of the acquired power as a random variable; and a correspondence degree determination means configured to determine whether a correspondence degree representing a degree of correspondence between the power acquired by the power acquisition means in a case that a predetermined reference speech signal is inputted into the power acquisition means and predetermined reference power is higher than a predetermined reference correspondence degree, based on the acquired probability distribution.

According to this, the speech signal processing device determines whether the power acquired in a case that the reference speech signal is inputted corresponds with the reference power based on the probability distributions with the intensity of the acquired power as a random variable. Consequently, it is possible to determine with high accuracy whether the power acquired in a case that the reference speech signal is inputted corresponds with the reference power.

In this case, it is preferred that:

the power acquisition means is configured to divide the accepted speech signal by a predetermined frame interval and acquire the power with respect to each portion of the divided speech signal; and the probability distribution acquisition means is configured to acquire the probability distribution based on the power acquired with respect to respective portions of the divided speech signal.

In this case, it is preferred that the correspondence degree determination means is configured to acquire a distribution distance value that becomes smaller as a degree of correspondence between the acquired probability distribution and a predetermined reference probability distribution becomes higher and, in a case that the acquired distribution distance value is smaller than a preset reference distance value, determine that the correspondence degree is higher than the reference correspondence degree.

In this case, it is preferred that:

the power acquisition means is configured to acquire the power for each frequency; and the probability distribution acquisition means is configured to acquire the probability distribution for each predetermined frequency range.

Probability distributions with the intensity of power as a random variable vary with frequency range. Therefore, by configuring the speech signal processing device as described above, it is possible to determine with higher accuracy whether the power acquired in a case that the reference speech signal is inputted corresponds with the reference power.

In this case, it is preferred that:

the power acquisition means is configured to correct the acquired power so as to be closer to the reference power;

the probability distribution acquisition means is configured to acquire the probability distribution based on the corrected power; and the correspondence degree determination means is configured to determine whether a correspondence degree representing a degree of correspondence between the power corrected by the power acquisition means in a case that the reference speech signal is inputted into the power acquisition means and the reference power is higher than the reference correspondence degree, based on the acquired probability distribution.

According to this, it is possible to determine with high accuracy whether the power corrected by the power acquisition means in a case that the reference speech signal is inputted into the power acquisition means corresponds with the reference power. In other words, it is possible to determine whether the power is properly corrected by the power acquisition means.

In this case, it is preferred that the probability distribution acquisition means is configured to estimate a probability density function, which is a function representing the probability distribution and is a function continuously changing with respect to the random variable, and thereby acquire the probability distribution.

In this case, it is preferred that the probability density function is a function that monotonically increases as the random variable increases from 0 to a predetermined peak position value and that monotonically decreases as the random variable increases from the peak position value.

In this case, it is preferred that the probability density function is a probability density function representing a gamma distribution A probability distribution with the power of background noise as a probability variable is well represented by a gamma distribution. Therefore, by configuring the speech signal processing device as described above, the speech signal processing device can estimate a probability density function that well represents a probability distribution with the intensity of power acquired by the power acquisition means as a random variable, in a case that a speech signal representing background noise is used as the reference speech signal.

In this case, it is preferred that the speech signal processing device is equipped with a plurality of microphones each configured to collect an ambient speech sound and output a speech signal representing the collected speech sound, and the power acquisition means is configured so that the speech signal outputted by each of the plurality of microphones is inputted thereinto.

In this case, it is preferred that the probability distribution acquisition means is configured to acquire a probability distribution with intensity of the power acquired by the power acquisition means based on the speech signal outputted by a first microphone of the plurality of microphones as a random variable, and the speech signal processing device is further equipped with a reference probability distribution acquisition means configured to acquire, as the reference probability distribution, a probability distribution with intensity of the power acquired by the power acquisition means based on the speech signal outputted by a second microphone of the plurality of microphones as a random variable.

Further, in another aspect of the speech signal processing device, it is preferred that the probability distribution acquisition means is configured to acquire a probability distribution with intensity of the power acquired by the power acquisition means based on the speech signal outputted by one of the plurality of microphones as a random variable, and the speech signal processing device is further equipped with a reference probability distribution acquisition means configured to acquire, as the reference probability distribution, a probability distribution with intensity of the power acquired by the power acquisition means based on the speech signal outputted by each of the plurality of microphones as a random variable.

In this case, it is preferred that:

the probability distribution acquisition means is configured to acquire a probability distribution with intensity of the power acquired by the power acquisition means based on the speech signal outputted by one of the plurality of microphones as a random variable; and the correspondence degree determination means is configured to use a previously stored value as the reference probability distribution.

Further, a speech signal processing method of another embodiment of the present invention is a method including:

accepting an inputted speech signal and, based on the accepted speech signal, acquiring power representing intensity of a speech sound represented by the speech signal;

acquiring a probability distribution with intensity of the acquired power as a random variable; and determining whether a correspondence degree representing a degree of correspondence between the power acquired by input of a predetermined reference speech signal and predetermined reference power is higher than a predetermined reference correspondence degree, based on the acquired probability distribution.

In this case, it is preferred that the speech signal processing method includes:

dividing the accepted speech signal by a predetermined frame interval and acquiring the power with respect to each portion of the divided speech signal; and acquiring the probability distribution based on the power acquired with respect to respective portions of the divided speech signal.

In this case, it is preferred that the speech signal processing method includes acquiring a distribution distance value that becomes smaller as a degree of correspondence between the acquired probability distribution and a predetermined reference probability distribution becomes higher and, in a case that the acquired distribution distance value is smaller than a preset reference distance value, determining that the correspondence degree is higher than the reference correspondence degree.

Further, a speech signal processing program of another embodiment of the present invention is a program including instructions for causing a speech signal processing device to realize:

a power acquisition means configured to accept an inputted speech signal and, based on the accepted speech signal, acquire power representing intensity of a speech sound represented by the speech signal;

a probability distribution acquisition means configured to acquire a probability distribution with intensity of the acquired power as a random variable; and a correspondence degree determination means configured to determine whether a correspondence degree representing a degree of correspondence between the power acquired by the power acquisition means in a case that a predetermined reference speech signal is inputted into the power acquisition means and predetermined reference power is higher than a predetermined reference correspondence degree, based on the acquired probability distribution.

In this case, it is preferred that the power acquisition means is configured to divide the accepted speech signal by a predetermined frame interval and acquire the power with respect to each portion of the divided speech signal; and the probability distribution acquisition means is configured to acquire the probability distribution based on the power acquired with respect to respective portions of the divided speech signal.

In this case, it is preferred that the correspondence degree determination means is configured to acquire a distribution distance value that becomes smaller as a degree of correspondence between the acquired probability distribution and a predetermined reference probability distribution becomes higher and, in a case that the acquired distribution distance value is smaller than a preset reference distance value, determine that the correspondence degree is higher than the reference correspondence degree.

Inventions of a speech signal processing method and a speech signal processing program having the abovementioned configurations also have actions like those of the speech signal processing device, and therefore, can achieve the abovementioned object of the present invention.

Below, exemplary embodiments of a speech signal processing device, a speech signal processing method and a speech signal processing program according to the present invention will be described with reference to FIGS. 1 to 6.

First Exemplary Embodiment (Configuration)

As shown in FIG. 1, a speech signal processing device 1 according to a first exemplary embodiment is an information processing device. The speech signal processing device 1 is equipped with a central processing unit (CPU), a storage device (a memory and a hard disk drive (HDD)) and an input device, which are not shown in the drawings.

The input device is connected to a plurality of (in this embodiment, six) microphones MC1 to MC6. Each of the microphones MC1 to MC6 collects ambient speech sounds, and outputs speech signals representing the collected speech sounds to the input device. The speech signals outputted by each of the microphones MC1 to MC6 are inputted into the input device, and the input device accepts the inputted speech signals. The input device configures part of a power acquisition means.

A function of the speech signal processing device 1 configured as described above is realized by execution of, for example, a speech signal processing program represented by a flowchart shown in FIG. 2 described later by the CPU of the speech signal processing device 1. This function may be realized by hardware such as a logical circuit.

This speech signal processing device 1 operates in a similar manner for each of the plurality of microphones MC1 to MC6. Therefore, the function and operation of the speech signal processing device 1 for any one microphone MCk (herein, k represents an integer of 1 to 6) of the plurality of microphones MC1 to MC6 will be described below.

The function of this speech signal processing device 1 includes a power acquisition unit (a power acquisition means) 10, a probability distribution acquisition unit (a probability distribution acquisition means, a reference probability distribution acquisition means) 20, and a correspondence degree determination unit (a correspondence degree determination means) 30.

The power acquisition unit 10 accepts a speech signal inputted from the microphone MCk. The power acquisition unit 10 converts the speech signal from an analog signal to a digital signal by executing an A/D (analog to digital) conversion process on the accepted speech signal.

Moreover, the power acquisition unit 10 divides the converted speech signal by a predetermined (in this embodiment, constant) frame internal. The power acquisition unit 10 executes the following process on each portion (a frame signal) of the divided speech signal.

The power acquisition unit 10 executes predetermined preprocessing (pre-emphasis, windowing of multiplying by a window function, and the like) on a frame signal. Next, the power acquisition unit 10 executes fast Fourier transform (FFT) on the frame signal, thereby acquiring a frame signal (a complex number including a real part and an imaginary part) in a frequency domain.

Then, for each frequency, the power acquisition unit 10 calculates the sum of a value obtained by squaring the real part of the acquired frame signal and a value obtained by squaring the imaginary part of the acquired frame signal, as power (the power of the speech signal).

For example, in a case that a signal obtained by sampling at a frequency of 44.1 kHz and 16-bit quantization is used as a digital signal, a frame interval is 10 ms and 1024-point FFT is executed, power $x_i(t)$ per approximately 43 Hz is calculated. Herein, i is a number corresponding to a frequency (in this embodiment, increase of i by 1 corresponds to increase of a frequency by approximately 43 Hz), and t is a number representing a position of a frame signal on the time axis (e.g., a frame number for specifying a frame).

Thus, the power acquisition unit 10 divides a speech signal accepted via the microphone MCk by a predetermined frame interval and, for each frequency, calculates power with respect to each portion (a frame signal) of the divided speech signal.

The power acquisition unit 10 corrects the calculated power $x_i(t)$ based on the following equation 1 so as to be closer to predetermined reference power. That is to say, for each frequency, the power acquisition unit 10 multiplies the calculated power $x_i(t)$ by a correction factor $f_i$ previously stored in the storage device, thereby correcting the power $x_i(t)$.

[Equation 1]

$$y_i(t)=f_i x_i(t) \quad (1)$$

Then, the power acquisition unit 10 outputs the corrected power $y_i(t)$. The correction factor $f_i$ is a value set for each number i corresponding to a frequency (i.e., a frequency) and set for each information for specifying the microphones MC1 to MC6. The correction factor $f_i$ is set so that, as a result of correction of the calculated power $x_i(t)$, the power $x_i(t)$ becomes closer to the aforementioned reference power.

The probability distribution acquisition unit 20 acquires a probability distribution with the intensity of the power $y_i(t)$ outputted by the power acquisition unit 10 as a random variable. In other words, it is possible to say that the probability distribution acquisition unit 20 acquires a probability distribution based on the power corrected by the power acquisition unit 10.

To be specific, the probability distribution acquisition unit 20 is configured to acquire a probability distribution in a case that a speech signal accepted by the power acquisition unit 10 is a speech signal representing background noise and, on the contrary, is configured not to acquire a probability distribution in a case that a speech signal accepted by the power acquisition unit 10 is a speech signal representing a speech sound other than background noise. In this description, a speech signal representing background noise is also referred to as a reference speech signal.

Background noise is speech sounds collected by the microphones MC1 to MC6 in a state that a sound source does not exist near the microphones MC1 to MC6. In this embodiment, in a case that a value obtained by averaging the intensity of power $y_i(t)$ outputted by the power acquisition unit 10 for a predetermined time period is smaller than a preset threshold, the probability distribution acquisition unit 20 determines the speech signal accepted by the power acquisition unit 10 as a speech signal representing background noise.

Firstly, for each range of power set in advance, the probability distribution acquisition unit 20 counts the number of power $y_i(t)$ existing in the range (i.e., the frequency of appearance of power within the range) among power $y_i(t)$ outputted by the power acquisition unit 10.

FIGS. 3A to 3F are graphs each representing a probability distribution with the intensity of power of a speech signal inputted via each of the microphones MC1 to MC6 as a random variable. Bars in FIGS. 3A to 3F have lengths proportional to the frequency.

The probability distribution acquisition unit 20 counts the abovementioned frequency based on the power $y_i(t)$ acquired for each of a plurality of (in this embodiment, one hundred) frame signals (a plurality of portions of the divided speech signal). Therefore, in this embodiment, the probability distribution acquisition unit 20 counts the abovementioned frequency based on 51200 (=512×100) pieces of power $y_i(t)$.

The larger the number of frame signals that become the basis of power $y_i(t)$ used to count the frequency becomes, the smaller the statistical dispersion of the counted frequency becomes. On the other hand, the larger the number of the frame signals becomes, the higher a possibility that noise occurring unexpectedly is included in background noise becomes. Therefore, it is preferred that the number of frame signals that become the basis of power $y_i(t)$ used to count the frequency is a number corresponding to one second to ten seconds.

Next, the probability distribution acquisition unit 20 estimates a probability density function, which is a function representing the probability distribution and is a function continuously varying with respect to the random variable, based on the counted frequency. According to this, it is possible to reduce processing load for calculating a distribution distance value, which will be described later. Moreover, it is possible to easily acquire a probability distribution for a range that the frequency is not counted.

As shown in FIGS. 3A to 3F, the distribution of the frequency monotonically increases as a random variable increases from 0 to a predetermined peak position value, and monotonically decreases as the random variable increases from the peak position value. The distribution of the frequency (i.e., a probability distribution with the power of background noise as a random variable) is well represented by a gamma distribution. A gamma distribution is represented by a probability density function represented by the following equation 2.

[Equation 2]

$$P(y) = \frac{1}{\Gamma(\lambda)\sigma^{\lambda}} y^{\lambda-1} e^{\frac{-1}{\sigma} y} \tag{2}$$

A probability density function P(y) represented by the above equation 2 is a function that monotonically increases as a random variable y increases from 0 to a predetermined peak position value, and that monotonically decreases as the random variable y increases from the peak position value.

In the equation 2, power $y_i(t)$ after correction is given as the random variable y. Moreover, $\Gamma(\lambda)$ is a gamma function, $\lambda$ is a shape parameter of the gamma distribution, and $\sigma$ is a scale parameter of the gamma distribution.

To be specific, the probability distribution acquisition unit 20 estimates a probability density function by determining the shape parameter $\lambda$ and the scale parameter $\sigma$ based on the counted frequency. In this embodiment, the probability distribution acquisition unit 20 determines the shape parameter $\lambda$ and the scale parameter $\sigma$ by executing maximum likelihood estimation. Thus, the probability distribution acquisition unit 20 estimates a probability density function as shown by a solid line in each of FIGS. 3A to 3F.

That is to say, the probability distribution acquisition unit 20 is configured to estimate a probability density function, which is a function representing the probability distribution and is a function continuously varying with respect to the random variable, and thereby acquire the probability distribution.

The correspondence degree determination unit 30 calculates (acquires) a distribution distance value for each combination including any two of the microphones MC1 to MC6. The distribution distance value is a value that decreases as a degree of correspondence between a first probability distribution acquired by the probability distribution acquisition unit 20 and a second probability distribution acquired by the probability distribution acquisition unit 20 increases.

The first probability distribution is a probability distribution with, as a random variable, the intensity of power outputted by the power acquisition unit 10 based on a speech signal outputted by a first microphone forming a combination including any two of the microphones MC1 to MC6. A second probability distribution is a probability distribution (a reference probability distribution) with, as a random variable, the intensity of power outputted by the power acquisition unit 10 based on a speech signal outputted by a second microphone fowling the combination including the two of the microphones MC1 to MC6.

The correspondence degree determination unit 30 calculates a distribution distance value $D_{KL}$ based on the following equation 3. In this embodiment, the distribution distance value $D_{KL}$ is a value that is also referred to as KL (Kullback-Leibler) divergence. Herein, p(y) is a probability density function representing the first probability distribution, and q(y) is a probability density function representing the second probability distribution.

[Equation 3]

$$D_{KL}(p\|q) = \int_{-\infty}^{\infty} \left\{ p(y) \log \frac{p(y)}{q(y)} \right\} dy \tag{3}$$

The distribution distance value can be any value representing the degree of mutual correspondence of a plurality of probability distributions, and may be a value referred to as a Bhattacharyya distance.

Then, the correspondence degree determination unit 30 acquires the maximum value of the distribution distance value $D_{KL}$ calculated for each combination including any two of the microphones MC1 to MC6. Next, the correspondence degree determination unit 30 determines whether the acquired maximum value of the distribution distance value $D_{KL}$ is smaller than a preset reference distance value.

In a case that the acquired maximum value of the distribution distance value $D_{KL}$ is smaller than the reference distance value, the correspondence degree determination unit 30 determines that a correspondence degree is higher than a reference correspondence degree. The correspondence degree represents a degree of correspondence between power outputted by the power acquisition unit 10 in a case that the reference speech signal (i.e., the speech signal representing background noise) is inputted into the power acquisition unit 10 via the first microphone and power (reference power) outputted by the power acquisition unit 10 in a case that the reference speech signal is inputted into the power acquisition unit 10 via the second microphone.

Thus, it is possible to say that the correspondence determination unit 30 determines whether the correspondence degree is higher than the preset reference correspondence degree, based on the probability distribution acquired by the probability distribution acquisition unit 20.

In the case of determining that the correspondence degree is higher than the reference correspondence degree, the correspondence degree determination unit 30 outputs a normal signal representing that correction of power by the power acquisition unit 10 is normally executed. On the contrary, in the case of determining that the correspondence degree is lower than the reference correspondence degree, the correspondence degree determination unit 30 outputs an error signal representing that correction of power by the power acquisition unit 10 is not normally executed.

(Operation)

Next, an operation of the speech signal processing device 1 configured as described above will be described.

Figure 2:
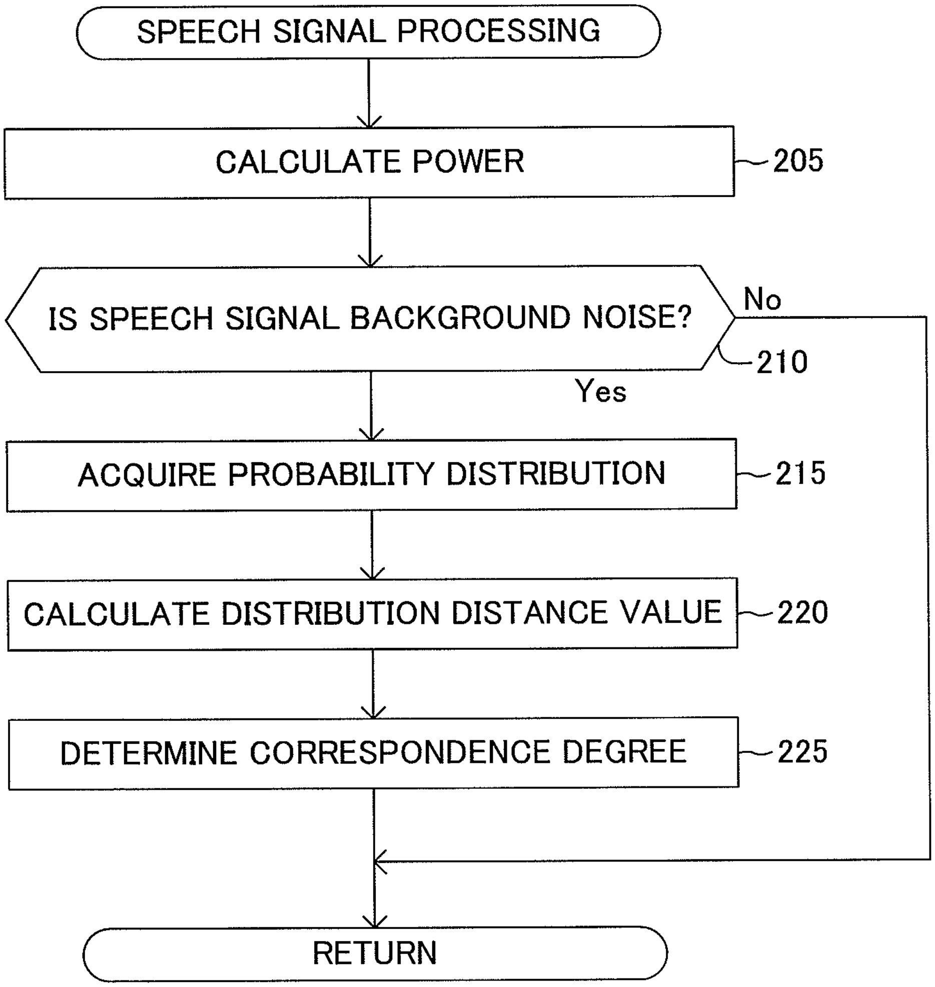
FIG. 2 is a flowchart showing a speech signal processing program executed by a CPU of the speech signal processing device shown in FIG. 1.
Figure 3:
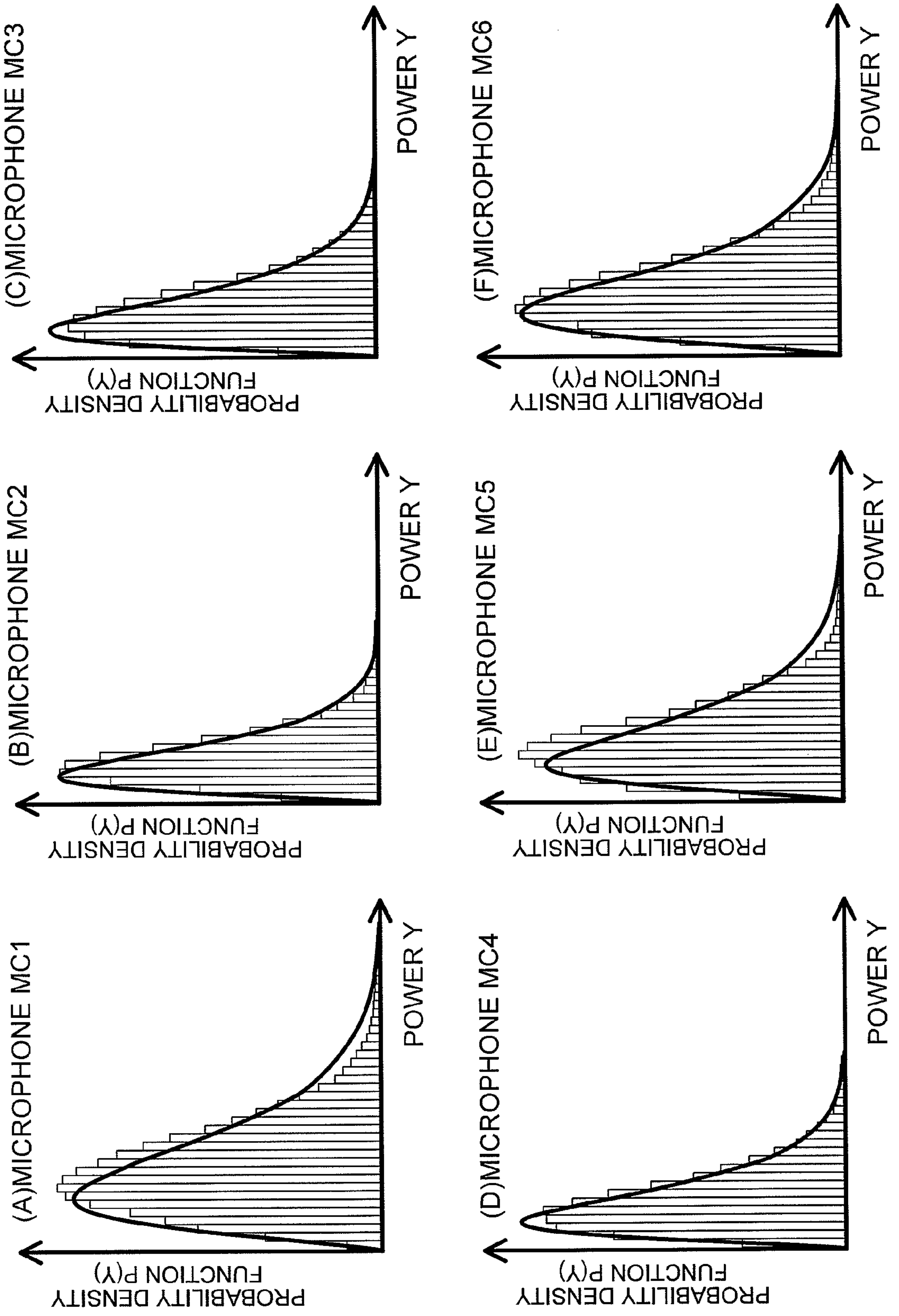
FIGS. 3A to 3F are graphs each showing a probability distribution with the intensity of power of a speech signal inputted via each of microphones as a random variable.

The CPU of the speech signal processing device 1 is configured to execute a speech signal processing program shown by a flowchart in FIG. 2, every time accepting a speech signal via the microphone MCk.

To be specific, upon start of a process of the speech signal processing program, at step 205, the CPU divides an accepted speech signal by a frame interval, and calculates power $x_i(t)$ for each portion (frame signal) of the divided speech signal. Moreover, the CPU corrects the calculated power $x_i(t)$ based on the equation 1, thereby calculating (acquires) power yi(t) after correction (a power acquisition step).

Next, at step 210, the CPU determines whether the accepted speech signal is a speech signal representing background noise.

Assuming the accepted speech signal is a speech signal representing background noise, the description will be continued. In this case, the CPU determines 'Yes' and proceeds to step 215.

Then, the CPU acquires a probability distribution with the intensity of the power $y_i(t)$ calculated at step 205 as a random variable.

To be specific, for each range of power set in advance, the CPU counts the number (the frequency) of the power $y_i(t)$ within the range among the calculated power $y_i(t)$. Then, based on the counted frequency, the CPU determines the shape parameter $\lambda$ and the scale parameter $\sigma$ of the gamma distribution, thereby estimating a probability density function represented by the equation 2. Thus, the CPU acquires a probability distribution with the intensity of the power $y_i(t)$ as a random variable (a probability distribution acquisition step).

Next, based on the acquired probability distribution and the equation 3, the CPU calculates the distribution distance value $D_{KL}$ for each combination including any two of the microphones MC1 to MC6 (step 220, part of a correspondence determination step).

Then, the CPU acquires the maximum value of the distribution distance value $D_{KL}$ calculated for each combination including any two of the microphones MC1 to MC6. Next, the CPU determines whether the acquired maximum value of the distribution distance value $D_{KL}$ is smaller than the reference distance value (in this embodiment, 0.01). Thus, the CPU determines whether the correspondence degree is higher than the reference correspondence degree (step 225, part of the correspondence determination step).

Figure 4:
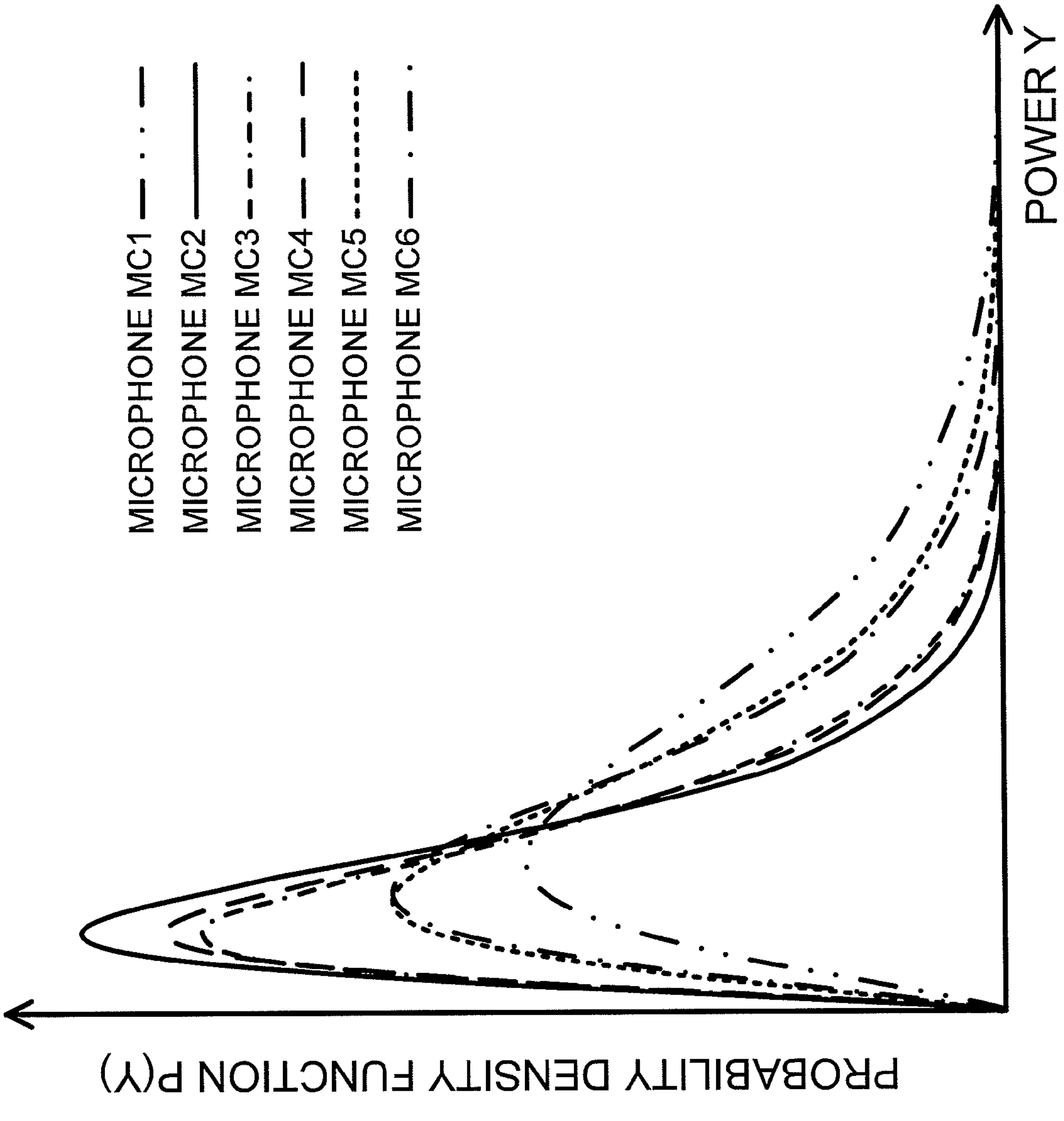
FIG. 4 is a graph showing probability distributions in a case that the probability distributions with respect to the respective microphones are relatively largely different from each other.

Assuming the probability distributions acquired for the respective microphones MC1 to MC6 are relatively largely different from each other as shown in FIG. 4, the description will be continued. In this embodiment, the maximum value of the distribution distance value $D_{KL}$ is 4.5. Therefore, in this case, the CPU determines that the correspondence degree is lower than the reference correspondence degree, and outputs an error signal. After that, the CPU ends execution of the speech signal processing program.

Figure 5:
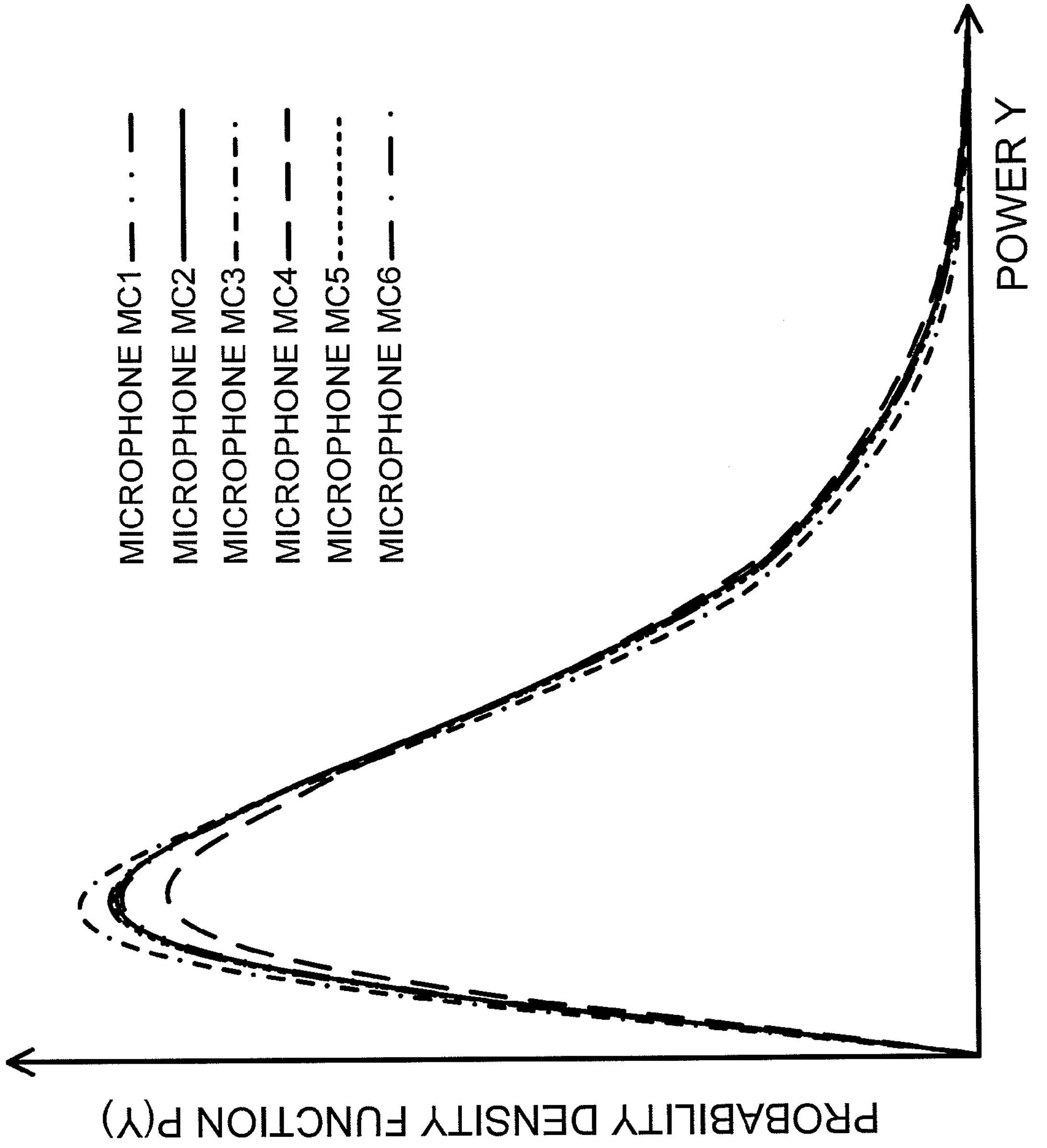
FIG. 5 is a graph showing probability distributions in a case that the probability distributions with respect to the respective microphones substantially correspond with each other.

Next, assuming the probability distributions acquired for the respective microphones MC1 to MC6 are substantially correspondent with each other as shown in FIG. 5, the description will be continued. In this embodiment, the maximum value of the distribution distance value $D_{KL}$ is 0.0044. Therefore, in this case, the CPU determines that the correspondence degree is higher than the reference correspondence degree, and outputs a normal signal. After that, the CPU ends execution of the speech signal processing program.

In a case that the accepted speech signal is not a speech signal representing background noise, the CPU determines 'No' at step 210, and ends execution of the speech signal processing program without executing the process from step 215 to step 225.

As described above, according to the first exemplary embodiment of the speech signal processing device of the present invention, the speech signal processing device 1 determines whether power acquired in a case that the reference speech signal is inputted via the first microphone and power (reference power) acquired in a case that the reference speech signal is inputted via the second microphone correspond with each other, based on a probability distribution with the intensity of acquired power as a random variable. Consequently, it is possible to determine with high accuracy whether the power acquired in a case that the reference speech signal is inputted and the reference power correspond with each other.

Further, in the first exemplary embodiment, the speech signal processing device 1 is configured to acquire a probability distribution based on corrected power and determine whether the correspondence degree is higher than the reference correspondence degree.

According to this, it is possible to determine with high accuracy whether power corrected by the power acquisition unit 10 in a case that the reference speech signal is inputted into the power acquisition unit 10 and the reference power correspond with each other. That is to say, it is possible to determine whether power is properly corrected by the power acquisition unit 10.

Further, in the first exemplary embodiment, the speech signal processing device 1 is configured to use a probability density function representing a gamma distribution, as a function representing a probability distribution with the intensity of power as a random variable. Thus, the speech signal processing device 1 can estimate a probability density function that well represents a probability distribution with the intensity of power as a random variable.

Second Exemplary Embodiment

Figure 6:
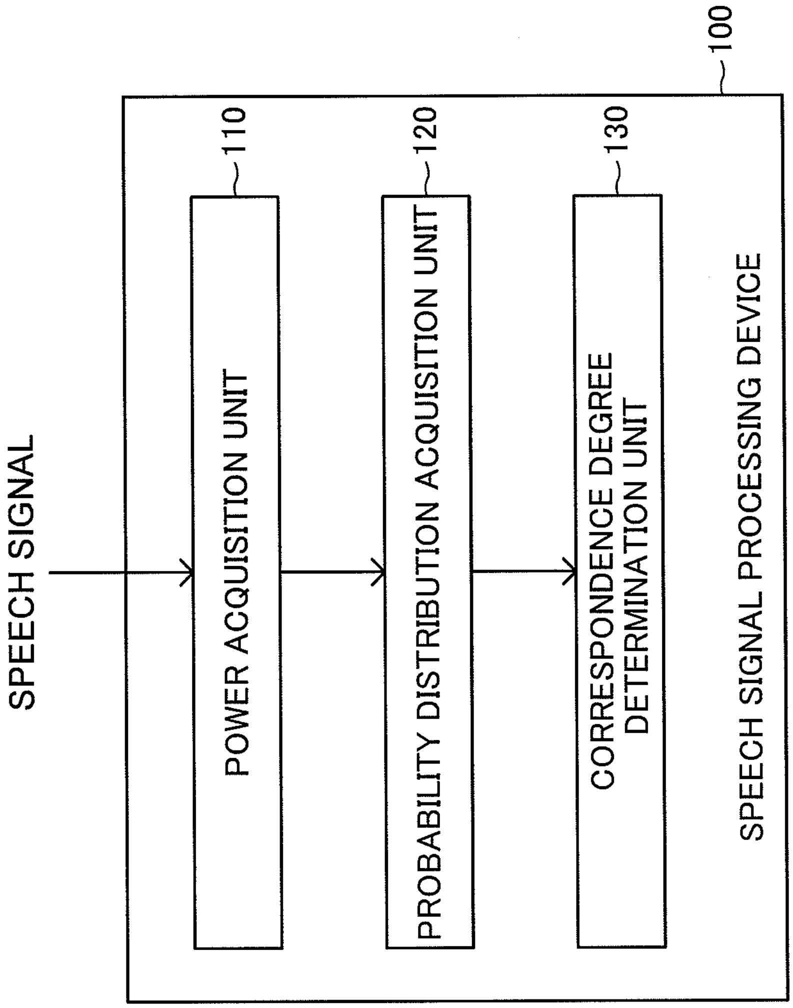
FIG. 6 is a block diagram schematically showing a function of a speech signal processing device according to a second exemplary embodiment of the present invention.

Next, a speech signal processing device according to a second exemplary embodiment of the present invention will be described with reference to FIG. 6.

A function of a speech signal processing device 100 according to the second exemplary embodiment includes a power acquisition unit (a power acquisition means) 110, a probability distribution acquisition unit (a probability distribution acquisition means) 120, and a correspondence degree determination unit (a correspondence degree determination means) 130.

The power acquisition unit 110 accepts an inputted speech signal and, based on the accepted speech signal, acquires power representing the intensity of a speech sound represented by the speech signal.

The probability distribution acquisition unit 120 acquires a probability distribution with the intensity of power acquired by the power acquisition unit 110 as a random variable.

The correspondence degree determination unit 130 determines whether a correspondence degree representing a degree of correspondence between power acquired by the power acquisition unit 110 in a case that a predetermined reference speech signal is inputted into the power acquisition unit 110 and predetermined reference power is higher than a predetermined reference correspondence degree, based on the probability distribution acquired by the probability distribution acquisition unit 120.

According to the speech signal processing device 100 of the second exemplary embodiment, the speech signal processing device 100 determines whether power acquired in a case that a reference speech signal is inputted corresponds with reference power, based on a probability distribution with the intensity of acquired power as a random variable. Consequently, it is possible to determine with high accuracy whether power acquired in a case that a reference speech signal is inputted corresponds with reference power.

Although the present invention is described above with reference to the respective exemplary embodiments, the present invention is not limited to the exemplary embodiments described above. The configuration and details of the present invention can be altered in various manners that can be understood by one skilled in the art within the scope of the present invention.

For example, in the exemplary embodiments described above, the probability distribution acquisition unit 20 may be configured to acquire a probability distribution for each predetermined frequency range. A probability distribution with the intensity of power as a random variable varies with a frequency range. Therefore, by thus configuring a speech signal processing device, it is possible to determine with higher accuracy whether power acquired in a case that a reference speech signal is inputted corresponds with reference power.

In a modified example of the exemplary embodiments described above, the probability distribution acquisition unit 20 may be configured not to estimate a probability density function but to use the counted frequency as a probability distribution. Moreover, the probability distribution acquisition unit 20 is configured to use a probability density function representing a gamma distribution as a function representing a probability function, but may be configured to use a probability density function representing a distribution (e.g., a normal distribution) other than a gamma distribution.

Further, in a modified example of the exemplary embodiments described above, the speech signal processing device 1 may be configured to prompt a user to reset the correction factor $f_i$ in the case of determining that the correspondence degree is lower than a reference correspondence degree. Moreover, the speech signal processing device 1 may be configured to change the correction factor $f_i$ in the case of determining that the correspondence degree is lower than a reference correspondence degree.

Further, in the exemplary embodiments described above, the speech signal processing device 1 is configured to calculate a distribution distance value for all of the combinations each including any two of the microphones MC1 to MC6 and determine whether the correspondence degree is higher than a reference correspondence degree based on the maximum value of the calculated distribution distance values.

In a modified example of the exemplary embodiments described above, the speech signal processing device 1 may be configured to define one of the microphones MC1 to MC6 as a reference microphone, calculate a distribution distance value for a combination of the reference microphone and each of the microphones MC1 to MC6 other than the reference microphone, and determine whether the correspondence degree is higher than a reference correspondence degree based on the maximum value of the calculated distribution distance values.

Further, in the exemplary embodiments described above, the speech signal processing device 1 is configured to determine whether the correspondence degree is higher than a reference correspondence degree based on the maximum value of the calculated distribution distance values, but may be configured to determine whether the correspondence degree is higher than a reference correspondence degree based on the average of the calculated distribution distance values.

Further, in the exemplary embodiment described above, the speech signal processing device 1 is configured to determine whether the correspondence degree is higher than a reference correspondence degree based on power after correction, but may be configured to determine whether the correspondence value is higher than a reference correspondence degree based on power before correction. According to this, it is possible to determine whether the frequency characteristics of the microphones MC1 to MC6 correspond.

Further, in the exemplary embodiments described above, the number of the microphones included by the speech signal processing device 1 is six, but may be any number of one or more.

Further, in the exemplary embodiments described above, the probability distribution acquisition unit 20 is configured to acquire, as a reference probability distribution, a probability distribution with the intensity of power acquired by the power acquisition unit 10 based on a speech signal outputted by one of the microphones as a random variable.

The probability distribution acquisition unit 20 may be configured to acquire, as a reference probability distribution, a probability distribution with the intensity of power acquired by the power acquisition unit 10 based on speech signals outputted by a plurality of microphones as a random variable. For example, the probability distribution acquisition unit 20 may be configured to acquire a reference probability distribution based on all the power acquired with respect to the plurality of microphones MC1 to MC6.

Further, the correspondence degree determination unit 30 may be configured to use a value previously stored in the storage device, as a reference probability distribution.

Further, in the exemplary embodiments described above, the probability distribution acquisition unit 20 is configured to acquire a probability distribution in a case that a speech sound represented by an accepted speech signal is background noise, but may be configured to acquire a probability distribution in a case that a speech sound represented by an accepted speech signal is a predetermined speech sound other than background noise.

Further, in the exemplary embodiments described above, the program is stored in the storage device, but may be stored in a computer-readable recording medium. For example, the recording medium is a portable medium such as a flexible disk, an optical disk, a magneto-optical disk and a semiconductor memory.

Further, as another modified example of the exemplary embodiments described above, any combination of the exemplary embodiments and modified examples described above may be employed.

The present invention is based upon and claims the benefit of priority from Japanese patent application No. 2009-065443, filed on Mar. 18, 2009, the disclosure of which is incorporated herein in its entirety by reference.

INDUSTRIAL APPLICABILITY

The present invention can be applied to, for example, a speech signal processing device equipped with a plurality of microphones and configured to accept speech signals inputted via the respective microphones and process the accepted speech signals.

DESCRIPTION OF REFERENCE NUMERALS

1 speech signal processing device
10 power acquisition unit
20 probability distribution acquisition unit
30 correspondence degree determination unit
100 speech signal processing device
110 power acquisition unit
120 probability distribution acquisition unit
130 correspondence degree determination unit
MC1 to MC6 microphones

The invention claimed is:

1. A speech signal processing device, comprising:

a power acquisition unit configured to accept an inputted speech signal and, based on the accepted speech signal, acquire power representing intensity of a speech sound represented by the speech signal;

a probability distribution acquisition unit configured to acquire a probability distribution with intensity of the acquired power as a random variable; and a correspondence degree determination unit configured to determine whether a correspondence degree representing a degree of correspondence between the power acquired by the power acquisition unit in a case that a predetermined reference speech signal is inputted into the power acquisition unit and predetermined reference power is higher than a predetermined reference correspondence degree, based on the acquired probability distribution, wherein the correspondence degree determination unit is configured to acquire a distribution distance value that becomes smaller as a degree of correspondence between the acquired probability distribution and a predetermined reference probability distribution becomes higher and, in a case that the acquired distribution distance value is smaller than a preset reference distance value, determine that the correspondence degree is higher than the reference correspondence degree.

2. The speech signal processing device according to claim 1, wherein:

the power acquisition unit is configured to divide the accepted speech signal by a predetermined frame interval and acquire the power with respect to each portion of the divided speech signal; and the probability distribution acquisition unit is configured to acquire the probability distribution based on the power acquired with respect to respective portions of the divided speech signal.

3. The speech signal processing device according to claim 1, wherein:

the power acquisition unit is configured to acquire the power for each frequency; and the probability distribution acquisition unit is configured to acquire the probability distribution for each predetermined frequency range.

4. The speech signal processing device according to claim 1, wherein:

the power acquisition unit is configured to correct the acquired power so as to be closer to the reference power;

the probability distribution acquisition unit is configured to acquire the probability distribution based on the corrected power; and the correspondence degree determination unit is configured to determine whether a correspondence degree representing a degree of correspondence between the power corrected by the power acquisition unit in a case that the reference speech signal is inputted into the power acquisition unit and the reference power is higher than the reference correspondence degree, based on the acquired probability distribution.

5. The speech signal processing device according to claim 1, wherein the probability distribution acquisition unit is configured to estimate a probability density function, which is a function representing the probability distribution and is a function continuously changing with respect to the random variable, and thereby acquire the probability distribution.

6. The speech signal processing device according to claim 5, wherein the probability density function is a function that monotonically increases as the random variable increases from 0 to a predetermined peak position value and that monotonically decreases as the random variable increases from the peak position value.

7. The speech signal processing device according to claim 6, wherein the probability density function is a probability density function representing a gamma distribution.

8. The speech signal processing device according to claim 1, comprising:

a plurality of microphones each configured to collect an ambient speech sound and output a speech signal representing the collected speech sound, wherein the power acquisition unit is configured so that the speech signal outputted by each of the plurality of microphones is inputted thereinto.

9. The speech signal processing device according to claim 8, wherein the probability distribution acquisition unit is configured to acquire a probability distribution with intensity of the power acquired by the power acquisition unit based on the speech signal outputted by a first microphone of the plurality of microphones as a random variable, the speech signal processing device further comprising:

a reference probability distribution acquisition unit configured to acquire, as the reference probability distribution, a probability distribution with intensity of the power acquired by the power acquisition unit based on the speech signal outputted by a second microphone of the plurality of microphones as a random variable.

10. The speech signal processing device according to claim 8, wherein the probability distribution acquisition unit is configured to acquire a probability distribution with intensity of the power acquired by the power acquisition unit based on the speech signal outputted by one of the plurality of microphones as a random variable, the speech signal processing device further comprising:

a reference probability distribution acquisition unit configured to acquire, as the reference probability distribution, a probability distribution with intensity of the power acquired by the power acquisition unit based on the speech signal outputted by each of the plurality of microphones as a random variable.

11. The speech signal processing device according to claim 1, wherein:

the probability distribution acquisition unit is configured to acquire a probability distribution with intensity of the power acquired by the power acquisition unit based on the speech signal outputted by one of the plurality of microphones as a random variable; and the correspondence degree determination unit is configured to use a previously stored value as the reference probability distribution.

12. A method of processing a speech signal using a speech signal processing device, the method comprising:

accepting an inputted speech signal and, based on the accepted speech signal, acquiring power representing intensity of a speech sound represented by the speech signal;

acquiring a probability distribution with intensity of the acquired power as a random variable;

determining whether a correspondence degree representing a degree of correspondence between the power acquired by input of a predetermined reference speech signal and predetermined reference power is higher than a predetermined reference correspondence degree, based on the acquired probability distribution; and acquiring a distribution distance value that becomes smaller as a degree of correspondence between the acquired probability distribution and a predetermined reference probability distribution becomes higher and, in a case that the acquired distribution distance value is smaller than a preset reference distance value, determining that the correspondence degree is higher than the reference correspondence degree.

13. The method according to claim 12, comprising:

dividing the accepted speech signal by a predetermined frame interval and acquiring the power with respect to each portion of the divided speech signal; and acquiring the probability distribution based on the power acquired with respect to respective portions of the divided speech signal.

14. A non-transitory computer-readable recording medium that records a speech signal processing program comprising instructions for causing a speech signal processing device to realize:

a power acquisition unit configured to accept an inputted speech signal and, based on the accepted speech signal, acquire power representing intensity of a speech sound represented by the speech signal;

a probability distribution acquisition unit configured to acquire a probability distribution with intensity of the acquired power as a random variable; and a correspondence degree determination unit configured to determine whether a correspondence degree representing a degree of correspondence between the power acquired by the power acquisition unit in a case that a predetermined reference speech signal is inputted into the power acquisition unit and predetermined reference power is higher than a predetermined reference correspondence degree, based on the acquired probability distribution, wherein the correspondence degree determination unit is configured to acquire a distribution distance value that becomes smaller as a degree of correspondence between the acquired probability distribution and a predetermined reference probability distribution becomes higher and, in a case that the acquired distribution distance value is smaller than a preset reference distance value, determine that the correspondence degree is higher than the reference correspondence degree.

15. The non-transitory recording medium according to claim 14, wherein:

the power acquisition unit is configured to divide the accepted speech signal by a predetermined frame interval and acquire the power with respect to each portion of the divided speech signal; and the probability distribution acquisition unit is configured to acquire the probability distribution based on the power acquired with respect to respective portions of the divided speech signal.

16. A speech signal processing device, comprising:

a power acquisition means configured to accept an inputted speech signal and, based on the accepted speech signal, acquire power representing intensity of a speech sound represented by the speech signal;

a probability distribution acquisition means configured to acquire a probability distribution with intensity of the acquired power as a random variable; and a correspondence degree determination means configured to determine whether a correspondence degree representing a degree of correspondence between the power acquired by the power acquisition means in a case that a predetermined reference speech signal is inputted into the power acquisition means and predetermined reference power is higher than a predetermined reference correspondence degree, based on the acquired probability distribution, wherein the correspondence degree determination means configured to acquire a distribution distance value that becomes smaller as a degree of correspondence between the acquired probability distribution and a predetermined reference probability distribution becomes higher and, in a case that the acquired distribution distance value is smaller than a preset reference distance value, determine that the correspondence degree is higher than the reference correspondence degree.

17. A speech signal processing device, comprising:

a power acquisition unit configured to accept an inputted speech signal and, based on the accepted speech signal, acquire power representing intensity of a speech sound represented by the speech signal;

a probability distribution acquisition unit configured to acquire a probability distribution with intensity of the acquired power as a random variable; and a correspondence degree determination unit configured to determine whether a correspondence degree representing a degree of correspondence between the power acquired by the power acquisition unit in a case that a predetermined reference speech signal is inputted into the power acquisition unit and predetermined reference power is higher than a predetermined reference correspondence degree, based on the acquired probability distribution, wherein the power acquisition unit is configured to correct the acquired power so as to be closer to the reference power;

the probability distribution acquisition unit is configured to acquire the probability distribution based on the corrected power; and the correspondence degree determination unit is configured to determine whether a correspondence degree representing a degree of correspondence between the power corrected by the power acquisition unit in a case that the reference speech signal is inputted into the power acquisition unit and the reference power is higher than the reference correspondence degree, based on the acquired probability distribution.

* * * * *